US00RE36008E

United States Patent [19]

Hindmarsh et al.

[11] E Patent Number: Re. 36,008

[45] Reissued Date of Patent: Dec. 22, 1998

[54] PROCESS FOR THE PRODUCTION OF TEREPHTHALIC ACID

[75] Inventors: Eric Hindmarsh, North Yorkshire; John Arthur Turner; David Parker, both of Middlesborough, all of England

[73] Assignee: E. I. du Pont de Nemours and Company, Wilmington, Del.

[21] Appl. No.: 634,991

[22] Filed: Apr. 19, 1996

Related U.S. Patent Documents

Reissue of:

[64] Patent No.: 5,304,676
Issued: Apr. 19, 1994
Appl. No.: 827,205
Filed: Jan. 30, 1992

[30] Foreign Application Priority Data

Feb. 5, 1991 [GB] United Kingdom ..... 9102393

[51] Int. Cl.[6] ..... C07C 51/215

[52] U.S. Cl. ..... 562/414; 562/487

[58] Field of Search ..... 562/414, 487

[56] References Cited

U.S. PATENT DOCUMENTS 2,849,483 8/1958 Ham .
3,452,088 6/1969 Olsen et al. .
3,592,847 7/1971 Gallivan et al. .
3,646,125 2/1972 Berthoux et al. .
4,467,111 8/1984 Puskas et al. .
4,933,492 6/1990 Schroeder et al. .
5,166,420 11/1992 Shiraki et al. .

FOREIGN PATENT DOCUMENTS 52-128344 10/1977 Japan .
970491 9/1964 United Kingdom .
970492 9/1964 United Kingdom .
1373230 11/1974 United Kingdom .

*Primary Examiner*—Samuel Barts
*Attorney, Agent, or Firm*—Pillsbury, Madison & Sutro, LLP Intellectual Property Group

[57] ABSTRACT

Terephthalic acid is produced by oxidation of para xylene, purified in an aqueous phase and recovered by precipitating a purified product from the aqueous phase, the aqueous phase mother liquor is then cooled or evaporated to produce a further less pure precipitate and a second mother liquor and the less pure precipitate is returned to the reaction medium and/or the water of the second mother liquor is used to dissolve the crude solid and/or the second mother liquor is treated to recover water which is used to wash the precipitate recovered from the aqueous solution. The process produces better yields of terephthalic acid, reduces the use of water and reduces problems in the disposal of polluted waste water.

15 Claims, 2 Drawing Sheets

PROCESS FOR THE PRODUCTION OF TEREPHTHALIC ACID

Matter enclosed in heavy brackets [ ] appears in the original patent but forms no part of this reissue specification; matter printed in italics indicates the additions made by reissue.

This invention relates to a process for the production of terephthalic acid.

In processes for the production of terephthalic acid by oxidation of p-xylene to terephthalic acid large quantities of for example demineralised water may used, especially as a solvent or wash liquid, during purification of the product. Such water becomes contaminated and may present problems of disposal and may, if it is discarded, involve a loss of potentially useful materials, especially terephthalic acid and/or its precursors.

Treatment of such water may be expensive and recovery of small quantities of impurities from it may be impractical.

This invention provides means by which water may be re-used within the process and useful materials recovered from it for example, in the form of an improved yield of terephthalic acid, without there being any significant reduction in the quantity of the pure terephthalic acid product.

According to this invention in a process in which p-xylene is oxidised to crude terephthalic acid product and in which the crude product is dissolved in a liquid comprising water, hydrogenated and cooled to precipitate a purified product which is separated from the liquid, after the separation step the said liquid is then cooled and/or evaporated to produce a further amount of precipitate, which is less pure than the purified product and which is recycled to the oxidation step. Suitably at least part of the liquid recovered from the second precipitation step is recycled and used directly or indirectly to dissolve the crude product.

The invention also comprises a process in which terephthalic acid is produced by oxidising para xylene to terephthalic acid is a liquid reaction medium which comprises acetic acid in which terephthalic acid is separated from the liquid reaction medium as a crude solid, dissolved in a liquid comprising water to produce a solution and purified by a process which comprises contacting the solution under reducing conditions with hydrogen and a heterogeneous catalyst for the reduction of at least some impurities, the solution is cooled after the acid reduction to precipitate solid purified terephthalic acid, aqueous mother liquor is separated from the precipitate and the precipitate is preferably washed with a liquid comprising water characterised in that the aqueous mother liquor is treated, for example cooled further and/or concentrated, to produce a less pure precipitate comprising terephthalic acid and a second mother liquor and at least one of the following steps is employed:

a) the less pure precipitate is returned preferably directly or indirectly to the reaction medium;
b) the water of the said second mother liquor is, directly as such or indirectly after treatment, used to dissolve the crude solid; and
c) the said second mother liquor is passed, desirably as reflux, to fractional distillation and treated water is recovered from the said distillation and is used to wash the precipitate recovered from the solution after the reduction step.

At least part of the aqueous mother liquor obtained from the precipitation of pure terephthalic acid may, directly as such or indirectly after treatment, be used to dissolve the crude solid and/or may be passed to fractional distillation and treated water is recovered from the said fractional distillation and is used to wash the precipitate recovered from the solution after the reduction step.

In order to control the temperature and/or water content of the reaction medium, a mixture of acetic acid and water is suitably removed from the reaction mixture by evaporation, water is fractionally distilled from the mixture and acetic acid is recycled directly or indirectly to the [machine] *reaction* medium.

The process requires that some material for example contaminated water should be purged to prevent build-up of unwanted contaminants in reaction streams, but substantial benefits arise from the invention nonetheless.

Recycling the less pure precipitate to the reaction medium enables further terephthalic acid to be recovered, and as some impurities, for example 4-carboxybenzoic acid and p-toluic acid, are oxidised to terephthalic acid the further yield of pure terephthalic acid in the process is beneficial.

Returning the second mother liquor as reflux to the fractional distillation is also beneficial in that its contaminants are generally high-boiling and pass with the acetic acid returned to the reaction into the reaction medium, in which they are also in at least some cases converted to terephthalic acid. As it is highly desirable to employ reflux in any case, a substantial amount of water may be treated at little cost.

The use of such treated water to dissolve the crude solid and/or to wash the precipitate recovered from solution after the reduction step and the use of the second mother liquor to dissolve the crude solid permits a significant reduction in the amount of fresh water that is required in the process and also the volume of contaminated water that is removed from the process as a purge. The reduced purge is in itself beneficial in that valuable contaminants for example, terephthalic acid precursor compounds and catalyst residues are not disposed of and in addition there is less waste effluent to be treated.

The invention may also permit re-optimization of the first precipitation step, after the reduction step so as to use higher temperatures and pressures for the precipitation step. Suitably the said precipitation step is operated at a pressure of more than 1 bar for example at least 3 bar, and suitably not more than 20 bar, preferably in the range 6 to 15 bar and especially in the range 7 to 12 bar for example 8 bar.

Precipitation at higher pressure and temperature reduces the amount of crystallization of impurities and the degree of co-crystallization of impurities with the terephthalic acid product. Thus the terephthalic acid product may be precipitated at a greater purity and the terephthalic acid remaining in solution can be largely recovered in the process of the invention.

The invention may also permit the re-optimization of the oxidation reaction step whereby a less pure crude terephthalic acid, characterised primarily by the 4-carboxybenzaldehyde content, may be put to the hydrogenation reaction step, as p-toluic acid so formed from the 4-carboxybenzaldehyde is substantially recovered and returned to the reaction medium where oxidation to terephthalic acid occurs. Hence a terephthalic acid of acceptable purity may be obtained from a process stream containing higher levels of impurities.

The present invention therefore allows the terephthalic acid production process to be optimised to provide greater product purity or to allow operation at greater impurity levels in the process stream as desired.

The individual steps of the process can be carried out conventionally. The liquid reaction medium normally comprises a catalyst, for example a cobalt/manganese/bromide catalyst system which is soluble in the reaction medium. Suitably the oxidation is carried out in the presence of an oxygen source for example air, at a pressure of 5 to 30 bars, and preferably an oxygen concentration of 0 to 8% in the gas leaving the reactor and at a temperature of 150° to 250° C. It is suitably a continuous process, and is preferably carried out in a stirred reactor. The reaction is exothermic and the heat of the reaction may conveniently be removed by evaporation of water and acetic acid from the reaction medium.

The heterogeneous catalyst employed in the purification of the crude terephthalic acid product may be a supported noble metal catalyst, for example platinum and/or preferably palladium on an inert, for example carbon, support. The purification is suitably carried out by passing the aqueous solution comprising terephthalic acid and impurities for example 4-carboxybenzaldehyde through a flooded bed of heterogeneous catalyst at a temperature of 250° to 350° C. in the presence of hydrogen. The solution suitably comprises 20 to 50% by weight of terephthalic acid.

The solution after reduction is suitably cooled to a temperature of 100° C. to 220° C., preferably 100° C. to 200° C. and pure terephthalic acid is suitably separated from the solution, which solution is subsequently cooled further, for example to 15° C. to 100° C., and/or evaporated to produce the less pure precipitate. The less pure precipitate is suitably separated from the aqueous mother liquor. The mother liquor from this separation, the second mother liquor, may be recycled directly or indirectly to the fractional distillation column and or to the reslurry of crude terephthalic acid.

The fractional distillation may be carried out at a reflux ratio of 2 to 10 and using 25 to 125 theoretical plates. The mother liquor returned to it may be fed for example at within 0 to 30% of the theoretical plates from the top of the column.

If evaporation is employed to produce the less pure precipitate this may be single or multiple effect evaporation suitably with sufficient reflux to minimise the passage of high boiling contaminants with the evaporated water.

Figure 1:
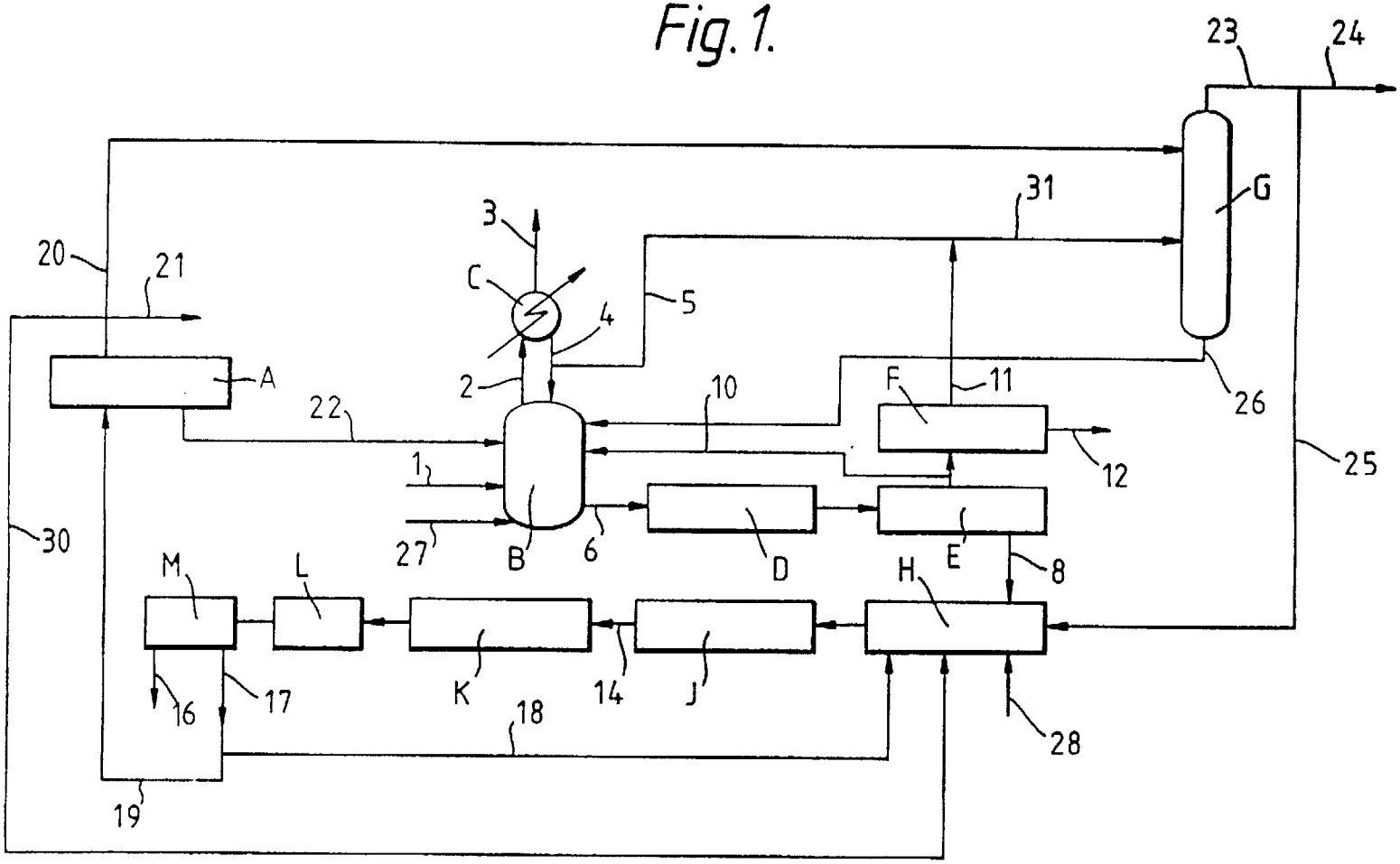
FIG. 1 is a flow diagram illustrating one embodiment of a process according to the present invention.

Reactor B is fed with paraxylene and acetic acid containing a dissolved catalyst comprising cobalt, manganese and bromide ions by line 1 and with air via line 27. Product from the reactor is passed to crystalliser D by line 6. The temperature within the reactor is controlled by evaporating a mixture of acetic acid and water from the reactor to a condensing system C via line 2. All or most of the condensate is returned to the reactor via line 4 with noncondensibles venting via line 3. In order to control the water content of the reaction vessel B, part of the condensate is removed from the condensing system via line 5 and passed to the distillation column G.

In the crystallization section D the temperature is dropped to approximately 75° C. to 120° C. and the slurry containing crystalline terephthalic acid in mother liquor thereby produced is passed to separator and drying stage E which is suitably a centrifuge or filter and a rotary or fluidised bed drier.

Mother liquor recovered from this stage is returned in part via line 10 to the reactor B usually by first mixing with the fresh catalyst, paraxlyene and acetic acid contained in stream 1. The remaining mother liquor is suitably passed to an evaporation stage F in which acetic acid is recovered by stream 11 to the distillation column G and/or via line 11 and line 26 back to the reactor B. A purge of by-products and other materials is withdrawn via stream 12.

From the separator and drying stage E solid terephthalic acid crystals are passed via stream 8 to a reslurry vessel H where the crystals are reslurried with water recovered from the distillation column via stream 25 and other water which may be recycle mother liquor via stream 18, recycle mother liquor via stream 30 and demineralised water via stream 28.

The slurry produced in this stage is heated in section J to a temperature of for example 250° C. to 350° C. to form a solution which is passed via stream 14 to reactor K in which it is reacted with hydrogen over a fixed bad palladium catalyst thus reducing impurities in the solution and then again crystallised in crystalliser L from which pure product is separated and dried in stage M which again is suitably a centrifuge or filter and rotary dried or fluidised bed drier.

The temperature to which the solution is cooled in the crystalliser and the rapidity of cooling is adjusted to produce the appropriate purity of the desired terephthalic acid product. The pure terephthalic acid product is recovered from stage M via line 16 and the mother liquor from the separation stage is passed via lines 17 and 19 to recovery stage A in which the liquid is evaporated or preferably further cooled so as to permit the recovery of further solids which may be passed back to reactor B via stream 22. The mother liquor recovered from A is at least in part passed back to the distillation column G and processed as described later and may in part be returned to the reslurry section H via stream 30 and may in part be purged via stream 21. Preferably if evaporation is used the evaporated water is returned to the reslurry stage H.

Figure 2:
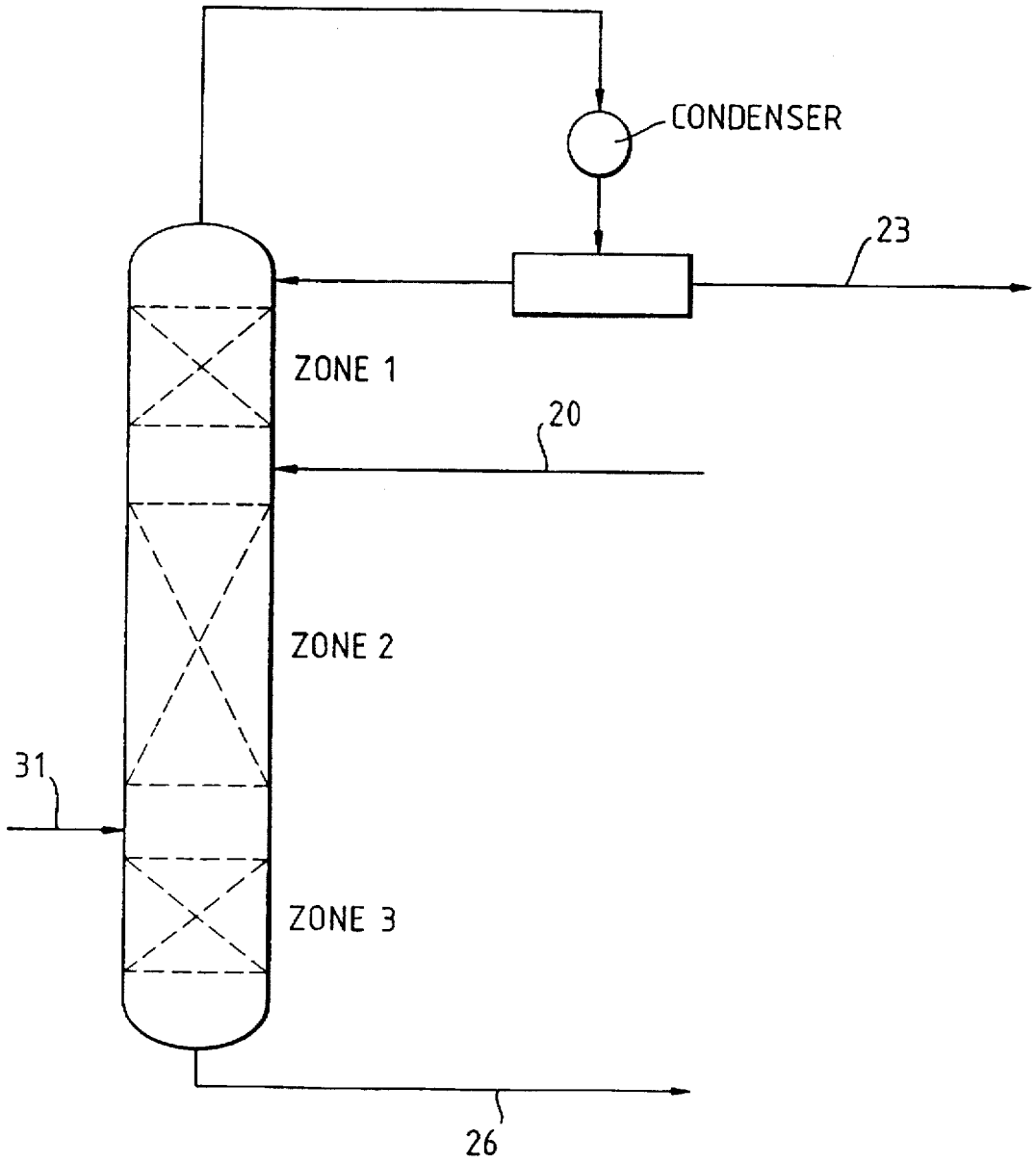
FIG. 2 is a schematic diagram illustrating a distillation column that can be used in the process illustrated by FIG. 1.

The distillation column G is shown in FIG. 2. The column fractionally distils a mixture of water and acetic acid evaporated from the reaction medium and has been modified for the treatment of mother liquor separated from precipitated mother liquor.

The column G comprises three zones; the upper Zone 1 comprises 5 theoretical stages, the middle Zone 2 comprises 40 theoretical stages and the lower Zone 3 comprises 10 theoretical stages.

A mixture of acetic acid and water evaporated from the reaction stage of oxidising p-xylene to terephthalic acid, streams 5 and 11 are passed via line 31 to between the middle and lower zones of the column. Mother liquor from the precipitation of terephthalic acid is passed into the column between the upper and middle zones via stream 20. Acetic acid and heavy material are passed from the base of the column via stream 26 to reactor B. Water is condensed in the condenser and reused in the process as aforesaid via stream 23.

When a feed of acetic acid and water is passed to the column between the middle and lower zones of the column and a reflux ratio of about 4 is maintained in the middle and lower zones of the column, it is found that the proportion of p-toluic acid and certain other impurities in the water removed from the column via stream 24 compared with the quantities present in the mother liquor fed to the column between the upper and middle zones via stream 20 is around 50% when the reflux ratio in the upper zone is zero and falls to less than 10% when the reflux ratio is 1.

The invention will now be illustrated with reference to the following non-limiting Examples.

EXAMPLE 1 (COMPARATIVE)

This is not an Example according to the invention. A mixture of p-xylene (1 part w/w) and acetic acid solvent (4.5 parts w/w) (containing water (4%)), cobalt and manganese (400 ppm w/w), and bromide (600 ppm w/w)) was fed at the rate of 5.5 parts w/w per hour into a semi-technical continuous oxidation reactor maintained at about 215° C. and 20 bars oxidised with sufficient air to maintain an oxygen concentration of about 3.5% v/v in the reactor off-gas, measured on a volatiles-free basis, with 1.5 parts w/w of condensate being removed per hour to control the reactor mother liquor water concentration and maintain it at a level of about 10% w/w. The terephthalic acid slurry leaving the reactor was fed to a second vessel maintained at about 190° C. and 17 bars and further oxidised whilst maintaining an oxygen concentration of about 5.5% v/v in the secondary oxidation reactor off-gas, measured on a volatiles-free basis. The slurry leaving the second vessel was let down in successive stages to atmospheric pressure, and periodically filtered, washed with acetic acid and then with water, and dried.

Reactor performance was monitored by on-line gas chromatography for carbon oxides, methyl acetate, p-xylene, and other trace components. After several hours at steady stage the reaction was terminated and the dried terephthalic acid samples analysed for purity by measurement of their 4-carboxybenzaldehyde (4CBA) content by HPLC and for their degree of powder colouration.

A series of such experiments was carried out to provide a range of results which gave a measure of experimental variability of the main performance parameters as listed in Table 1.

EXAMPLES 2

The procedure of Example 1 was repeated with the exception that an additional feed was added to the oxidation reactor feed mixture. This additional feed simulates the recycle of the impurities present in the mother liquor obtained on precipitating pure terephthalic acid from a pure terephthalic acid plant, that is a less pure precipitate obtained from the treatment for example by further cooling of the mother liquor obtained on precipitating pure terephthalic acid and the impurities contained in the mother liquor obtained from precipitating the less pure precipitate (second mother liquor).

The additional feed was of such composition as to provide a "worst case" recycle stream (complete return of the less pure precipitate and the mother liquor impurities). The composition of the additional feed was as follows (grams of component in the additional feed added to the oxidation reaction per 1000 g of p-xylene in the reaction feed);

| | |
|---|---|
| Terephthalic acid | 6.0 |
| p-Toluic acid | 1.6 |
| Byproducts and intermediates | 2.8 |
| Coloured compounds or precursor | 0.029 |
| Oxidation catalyst | 0.21 |

The results of this Example are shown in Table 1.

EXAMPLE 3

The procedure of Example 2 was repeated with the exception that the additional feed comprised the following components (grams of component in the additional feed added to the oxidation reaction per 1000 g of p-xylene in the reaction feed);

| | |
|---|---|
| Terephthalic acid | 8.5 |
| p-Toluic acid | 1.8 |
| Byproducts and intermediates | 0.7 |
| Coloured compounds or precursor | 0.013 |
| Oxidation catalyst | 0.002 |

The results of this Example are shown in Table 1.

TABLE 1

| | Example 1 (Comparative) | Example 2 | Example 3 |
|---|---|---|---|
| Degradation of acetic acid (te/te acetic acid) | 0.04 ≅ 0.002 | 0.0397 | 0.0403 |
| 4CBA content | 0.18 ± 0.02% | 0.186% | 0.180% |
| Colour (b*) | 5.6 ± 1.0 | 6.6 | 6.2 |

The results for Examples 2 and 3 were within the ranges observed for experiments performed according to Example 1 (Comparative).

Examples 2 and 3 demonstrate that the materials present in a less pure precipitate obtained from the filtrate obtained in precipitating the pure terephthalic acid may be recycled to the oxidation step without detrimental effect upon either quality of the crude terephthalic acid (and hence the pure terephthalic acid produced therefrom) or the oxidation performance. Furthermore, the yield of terephthalic acid is improved as at least some of the recycled terephthalic acid precursor compounds are oxidised to terephthalic acid.

The results show that by recycling less pure precipitate and the impurities contained in the mother liquor obtained from the second precipitation step the advantages of improved terephthalic acid yield reduced water usage and less waste affluent may be secured without any significant penalty as regards the quality of the pure terephthalic acid product.

We claim:

1. A process in which terephthalic acid is produced of oxidizing para xylene to terephthalic acid in a liquid reaction medium which comprises acetic acid and in which terephthalic acid is separated from the liquid reaction medium as a crude solid, dissolved in a liquid comprising water to produce a solution and purified by a process which comprises contacting the solution under reducing conditions with hydrogen and a heterogenous catalyst for the reduction of at least some impurities, the solution is cooled after said reduction to precipitate solid purified terephthalic acid, aqueous mother liquor is separated from the precipitate wherein;

a) the aqueous mother liquor is treated to produce a less pure precipitate comprising terephthalic acid and a second mother liquor;

b) the less pure precipitate is returned directly or indirectly to the reaction medium; and c) at least part of the said second mother liquor is, directly as such or indirectly after treatment, used to dissolve the crude solid.

2. A process in which terephthalic acid is produced by oxidizing para xylene to terephthalic acid in a liquid reaction medium which comprises acetic acid and in which terephthalic acid is separated from the liquid reaction medium as a crude solid, dissolved in a liquid comprising water to produce a solution and purified by a process which comprises contacting the solution under reducing conditions with hydrogen and a heterogenous catalyst for the reduction of at least some impurities, the solution is cooled after said reduction to precipitate solid purified terephthalic acid, aqueous mother liquor is separated from the precipitate wherein;

a) the aqueous mother liquor is treated to produce a less pure precipitate comprising terephthalic acid and a second mother liquor;

b) the less pure precipitate is returned directly or indirectly to the reaction medium;

c) at least part of the second mother liquor is subjected to fractional distillation to recover water from the second mother liquor; and d) the recovered water is used to wash the precipitate recovered from said solution after the reduction step.

3. A process according to claims [1 or 2] *1, 2, 9 or 10* in which, [in step a)], *in the step to produce a less pure precipitate* the mother liquor is cooled to a temperature within the range of 15° to 100° C. to produce said less pure precipitate.

4. A process according to claim 2 in which the fractional distillation (c) is carried out in a column at a reflux ratio of 2 to 10.

5. A process according to claim 4 in which 25 to 125 theoretical plates are used.

6. A process according to claim 4 in which the mother liquor returned to the fractional distillation is fed at within 0 to 30% of the theoretical plates from the top of the column.

7. A process according to [claim 1 or 2] *claims 1, 2, 9 or 10* in which the precipitation step to produce [pure] *purified* terephthalic acid is operated at a pressure of at least 3 bar.

8. A process according to claims [1 or 2] *1, 2, 9 or 10* in which, [in step a)] *in the step to produce a less pure precipitate,* the mother liquor is cooled to produce said less pure precipitate.

*9. A process for the production of terephthalic acid comprising:*

*in a first reactor oxidizing para xylene to terephthalic acid in a liquid reaction medium which comprises acetic acid, the reaction being accompanied by the evolution of vapor comprising acetic acid and water;*

*condensing said vapor and passing part of the condensate to a distillation column for separating acetic acid and water;*

*separating terephthalic acid from the liquid reaction medium as a crude solid;*

*dissolving the crude terephthalic acid in a liquid comprising water to produce a solution;*

*in a second reactor contacting the solution under reducing conditions with hydrogen and a heterogeneous catalyst for the reduction of at least some impurities;*

*cooling the solution after said reduction to precipitate solid purified terephthalic acid;*

*separating primary aqueous mother liquor from the precipitate;*

*treating the primary aqueous mother liquor to produce a less pure precipitate comprising terephthalic acid and a secondary mother liquor containing dissolved contaminants including p-toluic acid;*

*passing at least part of the secondary mother liquor to said distillation column for the separation of acetic acid from water;*

*operating the distillation column to produce a bottom product containing acetic acid from said condensate together with p-toluic acid and other high boiling point contaminants present in the secondary mother liquor and an overhead product comprising water derived from said condensate and said secondary mother liquor; and*

*supplying said bottom product to the first reactor.*

*10. A process as claimed in claim 9 further comprising returning the less pure precipitate directly or indirectly to the reaction medium.*

*11. A process as claimed in claim 9 or 10 comprising using at least part of the water derived from the distillation column to wash said precipitate comprising purified solid terephthalic acid.*

*12. A process as claimed in claim 9 or 10 comprising using at least part of the water derived from the distillation column in the dissolution of the crude terephthalic acid to produce said solution.*

*13. A process as claimed in claim 9 in which said distillation is carried out in a column at a reflux ratio of 20 to 10.*

*14. A process as claimed in claim 13 in which 25 to 125 theoretical plates are used in said distillation.*

*15. A process as claimed in claim 13 or 14 in which the secondary mother liquor is fed at within 0 to 30% of the theoretical plates from the top of the column.*

* * * * *